US00PP28071P3

(12) United States Plant Patent
Pierce

(10) Patent No.: US PP28,071 P3
(45) Date of Patent: May 30, 2017

(54) ***CALIBRACHOA* PLANT NAMED 'CBRZ0007'**

(50) Latin Name: ***Calibrachoa* Llave & Lex.**
Varietal Denomination: CBRZ0007

(71) Applicant: SYNGENTA PARTICIPATIONS AG, Basel (CH)

(72) Inventor: Robert O. Pierce, Watsonville, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/757,298

(22) Filed: Dec. 14, 2015

(65) Prior Publication Data

US 2016/0219778 P1 Jul. 28, 2016

Related U.S. Application Data

(60) Provisional application No. 62/106,843, filed on Jan. 23, 2015.

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — Dale Skalla

(57) ABSTRACT

A new *Calibrachoa* plant named 'CBRZ0007' particularly distinguished by the relatively large, burgundy flowers with a distinct dark-red ring or 'eye', medium green foliage, good branching, early to medium flowering, and a moderately compact, semi-trailing plant habit, and shows little sensitivity to soil pH.

1 Drawing Sheet

Latin name of the genus and species of the plant claimed: *Calibrachoa* Llave & Lex.

Varietal denomination: 'CBRZ0007'.

BACKGROUND OF THE NEW PLANT

The present invention comprises a new *Calibrachoa*, botanically known as *Calibrachoa hybrida*, and hereinafter referred to by the variety name 'CBRZ0007'.

'CBRZ0007' is a product of a planned breeding program. The new cultivar has relatively large, burgundy flowers with a distinct dark-red ring or 'eye', medium green foliage, good branching, early/medium flowering, and a moderately compact, semi-trailing plant habit, and shows little sensitivity to soil pH.

'CBRZ0007' originated from a hybridization made in December 2010 in a greenhouse in Gilroy, Calif., USA. The female parent was the unpatented proprietary plant designated 'MF PP×1319(3).1)-1'.

The male parent of 'CBRZ0007' was an unpatented proprietary plant identified as '(0513-2×1219-2)-1'.

The resulting seeds were sown in March 2011 and 'CBRZ0007' was selected as one flowering plant within the progeny of the stated cross in June 2011 in a controlled environment in Gilroy, Calif.

The first act of asexual reproduction of 'CBRZ0007' was accomplished when vegetative cuttings were propagated from the initial selection in the fall of 2011 in a controlled environment in Gilroy, Calif.

BRIEF SUMMARY OF INVENTION

Horticultural examination of plants grown from cuttings of the plant initiated in the spring of 2012, and continuing thereafter, has demonstrated that the combination of characteristics as herein disclosed for 'CBRZ0007' are firmly fixed and are retained through successive generations of asexual reproduction.

'CBRZ0007' has not been observed under all possible environmental conditions. The phenotype may vary significantly with variations in environment such as temperature, light intensity, and day length.

A Plant Breeder's Right for this cultivar was applied for in the European Community Plant Variety Office (CPVO) on Aug. 25, 2014, No. 2014/2074. 'CBRZ0007' has not been made publicly available more than one year prior to the filing of this application.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

Figure 1:
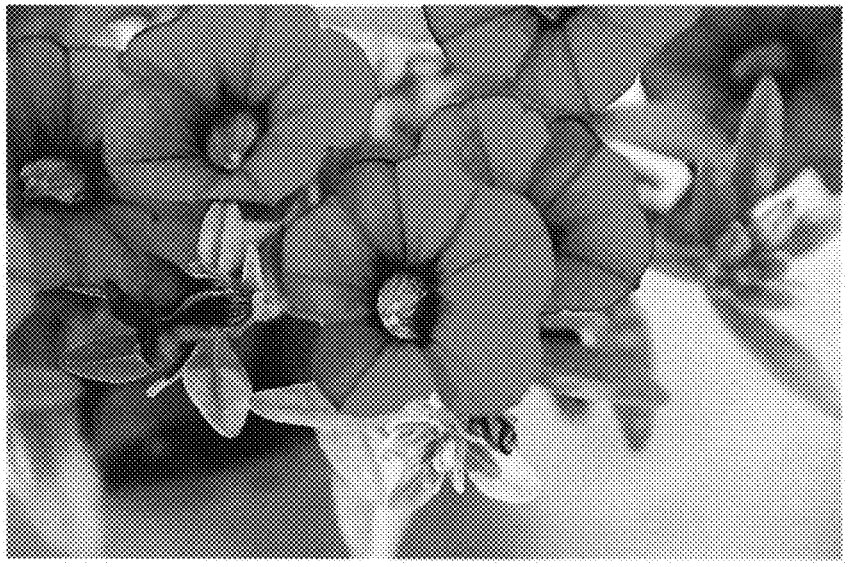
Figure 2:
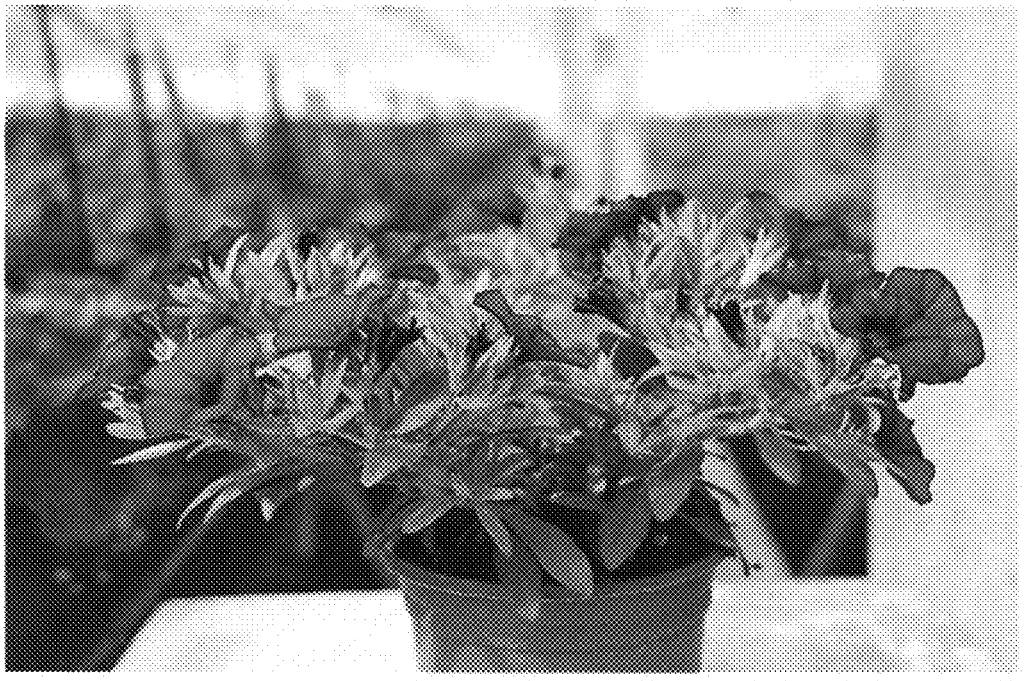

The accompanying photographic drawing shows typical flower and foliage characteristics of 'CBRZ0007' with colors being as true as possible with an illustration of this type. The photographic drawing shows in FIG. 1. a close-up of the flowers and in FIG. 2. a flowering plant of the new variety.

DETAILED BOTANICAL DESCRIPTION

The aforementioned photographs were taken outdoors on Jul. 14, 2014 in Andijk, the Netherlands. These plants were about 5-6 months of age.

Color references are made to The Royal Horticultural Society Colour Chart (R.H.S.) 2001.

TABLE 1

DIFFERENCES BETWEEN THE NEW VARIETY 'CBRZ0007' AND A SIMILAR VARIETY

| | 'CBRZ0007' | 'CAL BRITREEDA' (U.S. Plant Pat. No. 16,828) |
|---|---|---|
| Main flower color: | RHS 71A-B, more bluish than the comparison | RHS N57A |
| Flower, eye: | Narrow ring, RHS 187B, very dark purple | No distinct ring or eye |
| Flower diameter: | 3.8 cm | 3.0 cm |
| Plant habit: | Lower, more compact | Upright |
| Leaf, shape: | Narrower | Broader |

Plant:

*Form, growth and habit*.—Semi-upright stems, compact and mounding, very well branched.

*Plant height*.—9.5-12 cm; average 10.7 cm.

*Plant height* (*inflorescence included*).—About 11-13 cm.

*Plant width*.—18-21 cm; average 19.5 cm.

*Quantity of main branches*.—16-20.

*Quantity of secondary branches*.—4-6 per basal branch.

*Time to produce a flowering plant*.—7-8 weeks for a 12 cm pot (from planting of rooted cuttings).

Roots:

*Number of days to initiate*.—18-21 days at about 22° C.

*Number of days to produce a rooted cutting*.—21-24 days at 22° C.

*Type*.—Fibrous.

*Color*.—RHS 158D.

Stem:

*Color of stem*.—Mainly RHS 146C.

*Length of stem*.—Approximately 7-11 cm.

*Diameter*.—0.15-0.2 cm.

*Length of internodes*.—0.4-1.1 cm.

*Texture*.—Hair of various sizes, partly glandular hair.

Foliage:

*Immature leaf, color of upper surface*.—RHS 146A.

*Immature leaf, color of lower surface*.—RHS 144A.

*Mature leaf, color of upper surface*.—RHS 146A.

*Mature leaf, color of lower surface*.—Between RHS 146B and RHS 146C.

*Leaf blade, length*.—2.9-3.6 cm.

*Leaf, width*.—1.1-1.3 cm.

*Shape*.—Elliptical, narrow.

*Base shape*.—Acuminate.

*Apex shape*.—Obtuse.

*Margin*.—Entire.

*Texture*.—Both surfaces covered with dense, short hair, most distinct along the edge and the veins of the underside.

*Color of veins, upper surface*.—RHS 144A.

*Color of veins lower surface*.—RHS 144B.

*Petiole color*.—RHS 146C.

*Petiole length*.—0.1-0.3 cm.

*Diameter of petiole*.—0.2 cm.

*Texture*.—Both surfaces covered with dense, short hair.

Inflorescence:

*Type*.—Flowers solitary in upper leaf axis and slanting upright or outwards.

*Quantity of inflorescences per plant*.—Approximately 15-20.

*Lastingness of individual flowers*.—About 7-9 days.

*Fragrance*.—None.

*Duration of flowering*.—Continuous flowering throughout the summer.

Pedicel:

*Color of pedicel*.—RHS 143C.

*Length of pedicel*.—1.9-2.5 cm.

*Diameter of pedicel*.—0.1 cm.

*Texture of pedicel*.—Dense hair, partly glandular hair.

Flower:

*Immature flowers, corolla upper surface*.—RHS 67A base color.

*Immature flowers, corolla lower surface*.—RHS 71B.

*Mature flowers, color upper surface*.—Between RHS 71A and RHS 71B, with a somewhat deeper, purple-red ring, RHS 187B, in the centre around the throat opening.

*Mature flowers, color lower surface*.—RHS 71A to RHS 71B.

*Flower horizontal diameter*.—Up to 3.8 cm.

*Flower height* (*vertical*).—1.7-2.2 cm.

*Corolla tube length*.—1.3-1.6 cm.

*Petal apex shape*.—Truncate.

*Margin*.—Entire.

*Waviness of petals*.—Weak to medium.

*Petal lobation*.—Moderate.

*Corolla texture*.—'Face' papillose and glabrous; rear side with short hair along the veins.

*Corolla tube color inside*.—RHS 7C; RHS 152A veins, weak.

*Corolla tube color outside*.—RHS 154C to RHS 153D; fine, dark veins: RHS 177A.

Bud (just before opening):

*Color at apex*.—RHS N79B.

*Length*.—1.9-2.2 cm.

*Width* (*upper end*).—0.5-0.6 cm.

*Shape*.—Oblong.

Calyx:

*Number of sepals*.—5.

*Color of sepals, adaxial or upper surface*.—RHS 137C, slightly lighter basally.

*Color of sepals, abaxial or lower surface*.—RHS 137C to RHS 137D.

*Length of sepals*.—1.5-1.8 cm.

*Width of sepals*.—4-6 mm.

*Sepal shape*.—Lanceolate.

*Apex shape*.—Obtuse to acute.

*Margins*.—Entire.

*Texture*.—Glandular hairs of various sizes.

Reproductive organs:

*Pistil*.—1.

*Length*.—1.3 cm.

*Style color*.—RHS 145B.

*Style length*.—0.8-0.9 cm.

*Stigma color*.—RHS 144B.

*Number of stamens*.—5.

*Color of filaments*.—RHS 4D.

*Length filaments*.—0.7-1.1 cm.

*Color of pollen*.—RHS 13B.

*Pollen amount*.—Moderate.

*Fertility/seed set*.—Not observed on this hybrid.

Disease/pest resistance: Disease resistance or susceptibility has not been observed on this hybrid.

What is claimed is:

1. A new and distinct variety of *Calibrachoa* plant named 'CBRZ0007' substantially as illustrated and described herein.

* * * * *